United States Patent [19]

Novak et al.

[11] Patent Number: 5,032,380

[45] Date of Patent: Jul. 16, 1991

[54] DETECTION OF SULFUR MUSTARDS USING SPECTROFLUOROMETRY

[75] Inventors: Thaddeus Novak; Paul M. Davis, both of Bel Air, Md.

[73] Assignee: The United States of America as represented by the Secretary of the Army, Washington, D.C.

[21] Appl. No.: 488,180

[22] Filed: Mar. 5, 1990

[51] Int. Cl.$^5$ .................... G01N 21/64; G01N 31/22
[52] U.S. Cl. .................... 424/7.1; 426/120; 426/172; 568/56; 568/57; 568/68; 568/69
[58] Field of Search .................... 568/56, 57, 68, 69; 436/120, 172; 424/7.1

[56] References Cited

U.S. PATENT DOCUMENTS

| | | | |
|---|---|---|---|
| 2,054,885 | 9/1936 | Schoter | 568/56 |
| 2,797,246 | 6/1957 | Barber et al. | 568/56 |
| 4,414,414 | 11/1983 | Novak | 564/271 |
| 4,565,787 | 1/1986 | Bossle et al. | 436/120 |
| 4,913,897 | 4/1990 | Chvapil et al. | 424/91 |

FOREIGN PATENT DOCUMENTS 326982  1/1989  European Pat. Off. .

OTHER PUBLICATIONS

Klotz et al., Chemical Abstracts, vol. 41, 1946, Abstract 631b-d.
Meyer-Doring Z. anal Chem. 130, 234-4, 1950, Chemical Abstracts, vol. 44, 1950, Abstract 4830c-
Kimpflin, Chemical Abstracts, vol. 32, 1938, Abstract 5529.
Kuliev et al., Khim. Seraorg. Soedin., Soderzh. Neftyakh Nefteprod., 9, 172-8, Chemical Abstracts, vol. 79, 1973, Abstract 115348t.
Capomacchia et al., Anal. Chim. Acta 1974 73(1) 185-190 Chem. Abs., vol. 82, 1975, Abs. 9585v.
Carey and Sundberg, Advanced Organic Chemistry Part A, [New York Plenum Press, 1984], p. 266.

Primary Examiner—Mukund J. Shah
Assistant Examiner—E. C. Ward
Attorney, Agent, or Firm—Anthony T. Lane; Edward Goldberg; Edward F. Costigan

[57] ABSTRACT

Fluorescence properties of the product of the reaction of the 2-naphthalenethiolate ion and 2-chloroethylethylsulfide or bis(2-chloroethyl)sulfide are described. The fluorescence of the latter reaction is used as the basis of a new detection method for 2-chloroethylethylsulfide. The detection method is capable of detecting 2-chloroethylethylsulfide at levels down to 0.2 micrograms per milliliter.

1 Claim, 1 Drawing Sheet

REACTION PROFILE FOR REACTION AT 25°C OF 2-NAPHTHALENETHIOLATE ION IN AQUEOUS CHES BUFFER CONTAINING 4% METHANOL WITH THREE DIFFERENT LEVELS OF CEES. EXCITATION WAVELENGTH IS 254 nm.

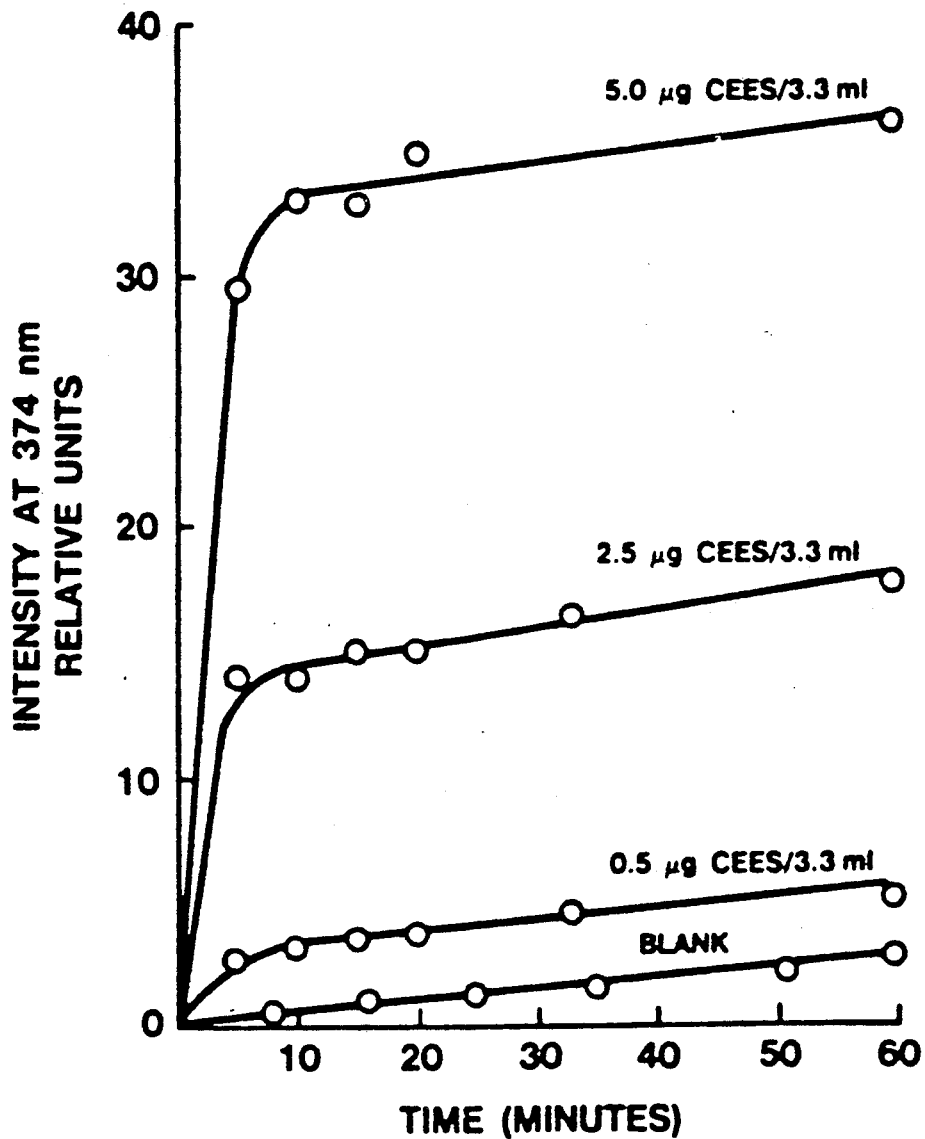
REACTION PROFILE FOR REACTION AT 25°C OF 2-NAPHTHALENETHIOLATE ION IN AQUEOUS CHES BUFFER CONTAINING 4% METHANOL WITH THREE DIFFERENT LEVELS OF CEES. EXCITATION WAVELENGTH IS 254 nm.

DETECTION OF SULFUR MUSTARDS USING SPECTROFLUOROMETRY

GOVERNMENTAL INTEREST

The invention described herein may be manufactured, used and licensed by or for the Government for governmental purposes without payment to us of any royalties thereon.

FIELD OF USE

This invention relates to the detection of 2-chloroethylethylsulfide, a simulant of toxic agents known as mustard, and bis(2-chloroethyl)sulfide which is mustard.

More particularly, this invention relates to the use of 2-naphthalenethiolate ion in the detection of 2-chloroethylethylsulfide and bis(2-chloroethyl)sulfide.

In the past, fiber optic waveguides have been known for use in the detection of toxins and nerve agents. However, there are no known fluorogenics that are used with a fiber optic waveguide for the detection of mustard or lewisite. 2-Chloroethylethylsulfid is a simulant for mustard and lewisite. Therefore, in accordance with regulations, this simulant is used in research to produce results which are acceptable for mustard and lewisite.

SUMMARY OF INVENTION

It is an object of this invention to provide the sensitive fluorogenic detection of either 2-chloroethylethylsulfide or bis(2-chloroethyl)sulfide.

Another object is to provide the reaction of 2-chloroethylethylsulfide or bis(2-chloroethyl)sulfide with 2-naphthalenethiola ion to produce a highly fluorescent product which may be detected by a fiber optic waveguide.

Other objects of this invention will become more apparent from a reading of the specification taken with a drawing wherein:

FIG. 1 contains reaction profiles at 25° C. of 2-naphthalenethiolate ion in a aqueous buffer containing 4% methanol with three different levels of 2-chloroethylethylsulfide. The excitation wavelength is 254 nm.

DETAILED DESCRIPTION OF PREFERRED EMBODIMENTS

Prepare a 2-naphthalenethiol solution in a 100-ml volumetric flask by dissolving 169.2 mg of 2-naphthalenethiol in methanol, and adding methanol to the mark. Dilute the stock solution 1:10 with methanol.

Prepare a working solution by diluting the stock solution 1:25 with distilled water.

Place the working solution (3.0 ml) in a 1 cm quartz fluorescence cell, and add 0.03 ml of aqueous (2-[N-cyclohexylamino]ethanesulfonic acid) buffer at 1 M and at pH 9.75. The buffer was adjusted to pH 9.75 with aqueous sodium hydroxide. Bring the temperature of the solution in the fluorescence cell to 25° C.

With the excitation wavelength at 254 nm, and the emission wavelength at 374 nm, read the fluorescence intensity for a reagent blank.

Add the 2-chloroethylethylsulfide, the simulant for mustard and lewisite, dissolved in acetonitrile (10 microliters) to the solution in the cell. Cap the cell, and mix the sample by inverting several times. Incubate the sample at 25° C. for 15 minutes.

With the excitation wavelength at 254 nm, and the emission wavelength at 374 nm, read the fluorescence intensity for the sample.

Calculate the net intensity of the fluorescence for the sample by subtracting the blank reading from the sample reading, and compare with a standard chart shown in FIG. 1.

In another preferred embodiment:

Prepare a 2-naphthalenethiol solution in a 100-ml volumetric flask by dissolving 169.2 mg of 2-naphthalenethiol in methanol, and adding methanol to the mark. Dilute the stock solution 1:10 with methanol.

Prepare a working solution by diluting the stock solution 1:25 with distilled water.

Place the working solution (3.0 ml) in a 1 cm quartz fluorescence cell, and add 0.03 ml of aqueous (2-[N-cyclohexylamino]ethanesulfonic acid) buffer at 1 M and at pH 9.75. The buffer was adjusted to pH 9.75 with aqueous sodium hydroxide. Bring the temperature of the solution in the fluorescence cell to 25° C.

With the excitation wavelength at 254 nm, and the emission wavelength at 374 nm, read the fluorogenic intensity for a reagent blank.

Add the bis(2-chloroethyl)sulfide, dissolved in acetonitrile (10 microliters) to the solution in the cell. Cap the cell, and mix the sample by inverting several times. Incubate the sample at 25° C. for 15 minutes.

With the excitation wavelength at 254 nm, and the emission wavelength at 374 nm, read the fluorescence intensity for the sample.

Calculate the net intensity of the fluorescence for the sample by subtracting the blank reading from the sample reading, and compare with a standard chart shown in FIG. 1.

In conclusion, this detection method is capable of detection of 2-chloroethylethylsulfide at final concentrations down to 0.2 micrograms per millimeter. Essentially the same results are obtained with bis(2-chloroethyl)sulfide which is also known as the toxic agent mustard.

What is claimed:

1. A fluorescense method comprising detecting bis (2-chloroethyl) sulfide and 2-chloroethylethylsulfide with 2-naphthalenethiolate by excitation at a wavelength of 254 nm to give a measurable peak emission at wavelength 374 nm.

* * * * *